(12) United States Patent
Osman

(10) Patent No.: US 8,702,709 B2
(45) Date of Patent: Apr. 22, 2014

(54) INTERVERTEBRAL DISC REAMER

(76) Inventor: Said G. Osman, Russellville, AL (US)

( * ) Notice: Subject to any disclaimer, the term of this patent is extended or adjusted under 35 U.S.C. 154(b) by 1504 days.

(21) Appl. No.: 12/210,651

(22) Filed: Sep. 15, 2008

(65) Prior Publication Data

US 2009/0076511 A1    Mar. 19, 2009

Related U.S. Application Data

(60) Provisional application No. 60/972,412, filed on Sep. 14, 2007.

(51) Int. Cl.
*A61B 17/00* (2006.01)

(52) U.S. Cl.
USPC .......................................................... 606/80

(58) Field of Classification Search
USPC ................................ 606/79–80; 408/127, 201
See application file for complete search history.

(56) References Cited

U.S. PATENT DOCUMENTS

| | | | | |
|---|---|---|---|---|
| 4,706,659 A | * | 11/1987 | Matthews et al. | 606/80 |
| 4,751,922 A | * | 6/1988 | DiPietropolo | 606/80 |
| 5,122,134 A | * | 6/1992 | Borzone et al. | 606/80 |
| 5,203,595 A | * | 4/1993 | Borzone et al. | 285/325 |
| 5,851,208 A | * | 12/1998 | Trott | 606/80 |
| 6,258,093 B1 | * | 7/2001 | Edwards et al. | 606/80 |
| 6,656,195 B2 | * | 12/2003 | Peters et al. | 606/159 |
| 2006/0015110 A1 | * | 1/2006 | Pepper | 606/80 |
| 2007/0225721 A1 | * | 9/2007 | Thelen et al. | 606/80 |

* cited by examiner

*Primary Examiner* — Nicholas Woodall
(74) *Attorney, Agent, or Firm* — Nixon & Vanderhye P.C.

(57) ABSTRACT

An intervertebral disc reamer includes a flexible shaft having a shaft channel, and a reamer head attached to the flexible shaft and movable relative to the flexible shaft. The reamer head has a reamer channel. The shaft channel and the reamer channel are aligned to define a continuous guide wire channel for the disc reamer. The disc reamer addresses the quality of disc removal and endplate preparation, minimizes the trauma of surgery, minimizes blood loss, and markedly reduces surgical time.

16 Claims, 7 Drawing Sheets

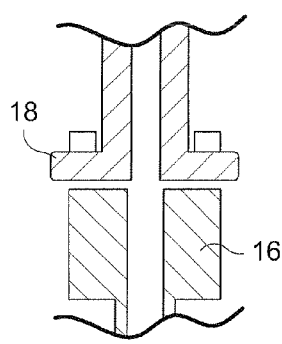
Fig. 3
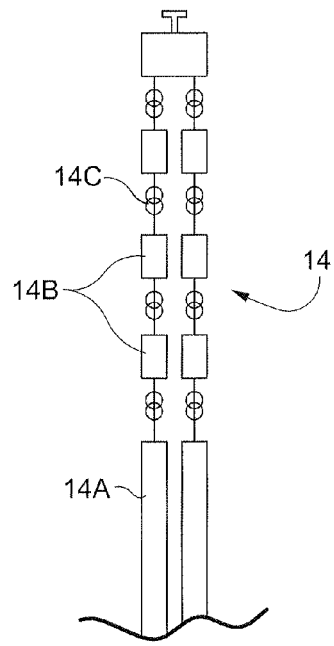
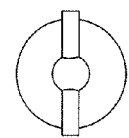
Fig. 4
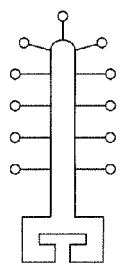
Fig. 5
Fig. 6
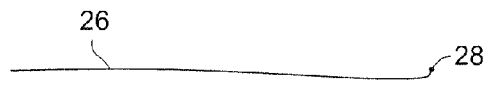
Fig. 7A
Fig. 7B

INTERVERTEBRAL DISC REAMER

CROSS-REFERENCES TO RELATED APPLICATIONS

This application claims the benefit of U.S. Provisional Patent Application Ser. No. 60/972,412, filed Sep. 14, 2007, the entire content of which is herein incorporated by reference.

STATEMENT REGARDING FEDERALLY SPONSORED RESEARCH OR DEVELOPMENT (Not Applicable)

BACKGROUND OF THE INVENTION

Thousands of spine procedures are performed daily in the United States and around the world. Many of these procedures involve removal of the disc material in preparation for either fusion or replacement of the disc. Meticulous disc space preparation is required for either fusion or disc replacement, and this task is invariably laborious and is often performed sub-optimally.

The variety of disc surgical procedures is rapidly increasing, keeping abreast with the progress of technology. Disc excision usually involves removal of the extruded nucleus material as well as the nuclear material lying loosely in the disc space. Partial disc replacements are in the early stages of evolution and involve variable amounts of nuclear material. Total disc replacements and fusion of the disc space involve removal of the nucleus, some annular material posteriorly, and the endplates to facilitate bonding of the prosthetic disc to the host bone, in the case of the disc replacement and incorporation of the bone graft, in the case of fusion. While it is possible to remove the endplates in a reproducible fashion through the open anterior approach, it is difficult to quantify the completeness of the disc excision through the posterior and transforaminal approaches. At this time there is no effective way of thoroughly excising the disc and preparing the end-plate through the least invasive approaches, such as the arthroscopic approach, for disc replacement or fusion.

It would be desirable to address the quality of disc removal and endplate preparation, while minimizing the trauma of surgery, minimizing blood loss, and markedly reducing surgical time.

BRIEF SUMMARY OF THE INVENTION

An intervertebral disc reamer includes various design versions for different approaches of disc surgery, including but not limited to arthroscopic disc excision and endplate preparation, transforaminal disc excision and endplate preparation, posterior lumbar interbody procedures, transverse lumbar interbody procedures, anterior interbody techniques, and the like. Safety of the device during surgery is ensured by preventing the operation of the disc reamer outside of the disc space by utilizing threaded cannulas that are locked into the vertebral endplates and by use of a flexible guide wire that controls the direction and depth of reaming under fluoroscopic control.

In an exemplary embodiment, an intervertebral disc reamer includes a flexible shaft having a shaft channel, and a reamer head attached to the flexible shaft and movable relative to the flexible shaft. The reamer head has a reamer channel. The shaft channel and the reamer channel are aligned to define a continuous guide wire channel for the disc reamer. In one arrangement, the flexible shaft is a one-piece member. Alternatively, the flexible shaft may include a plurality of shaft links connectable one to another, where a distal one of the shaft links is coupled with the reamer head, and where adjacent shaft links are movable in at least one plane relative to each other. In this context, the shaft links may be shaped as one of spherical, cylindrical and scalloped proximally and distally. Additionally, each of the shaft links may be cannulated. The shaft links may have a surface finish as one of smooth, fluted and curved, fluted straight, and a curved blade that propels disc debris back as the reamer head is advanced. The adjacent shaft links may be contoured to bias flexibility in at least one predefined plane while protecting the adjacent shaft links from debris.

In one arrangement, the reamer head is attached to the flexible shaft via a neck that has a narrow cross-section so as to facilitate flexibility of articulation.

The reamer head may be shaped as one of cylindrical, conical and spherical. In this context, the reamer head may have a surface finish as one of roughened, curved into cutting blades, and flexible pins tipped with small metal balls. The reamer head may be attached to the flexible shaft via one of a fixed connection, a ball and socket connection, and a T-shaped slot or bar coupled with a corresponding T-shaped bar or slot in a distal end of the flexible shaft.

The disc reamer may additionally include a reamer guide that is sized to fit in the guide wire channel. The reamer guide is formed of a flexible non-deforming construction.

In another exemplary embodiment, an intervertebral disc reamer includes a flexible shaft, a neck, and a reamer head. The flexible shaft is formed of a plurality of cannulated shaft links connectable one to another that define a shaft channel. The neck is movably secured to a distal shaft link of the flexible shaft. The reamer head is attached to the flexible shaft via the neck and is movable relative to the flexible shaft. The reamer head has a reamer channel, where the shaft channel and the reamer channel are aligned to define a continuous guide wire channel for the disc reamer.

In yet another exemplary embodiment, a method of inserting an intervertebral disc reamer includes the steps of securing threaded cannulas into a patient's disc space; introducing a reamer guide wire through the cannulas into the disc space; and inserting the disc reamer having a continuous guide wire channel over the reamer guide wire, wherein the disc reamer is flexible such that the disc reamer follows an orientation of the guide wire.

BRIEF DESCRIPTION OF THE DRAWINGS

These and other aspects and advantages will be described in detail with reference to the accompanying drawings, in which:

FIG. 3 is a close-up view one of the shaft links of the reamer shaft;

FIG. 4 is a cross-section of the shaft link;

FIG. 5 shows an exemplary reamer head;

FIG. 6 shows an alternative construction of the disc reamer;

FIGS. 7A and 7B show varying orientations of the reamer guide wire;

DETAILED DESCRIPTION OF THE INVENTION

Figure 1:
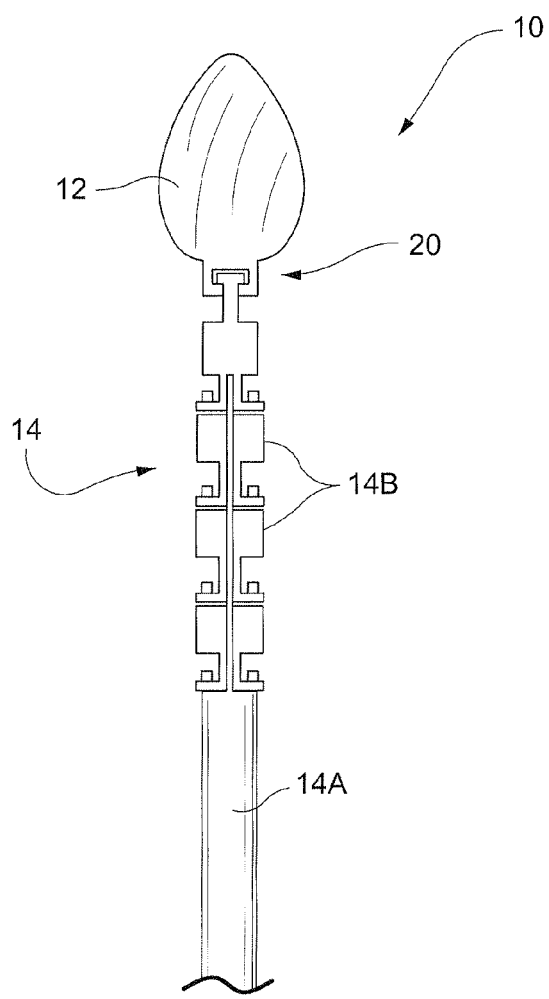
FIG. 1 shows the intervertebral disc reamer of a preferred construction.
Figure 2:
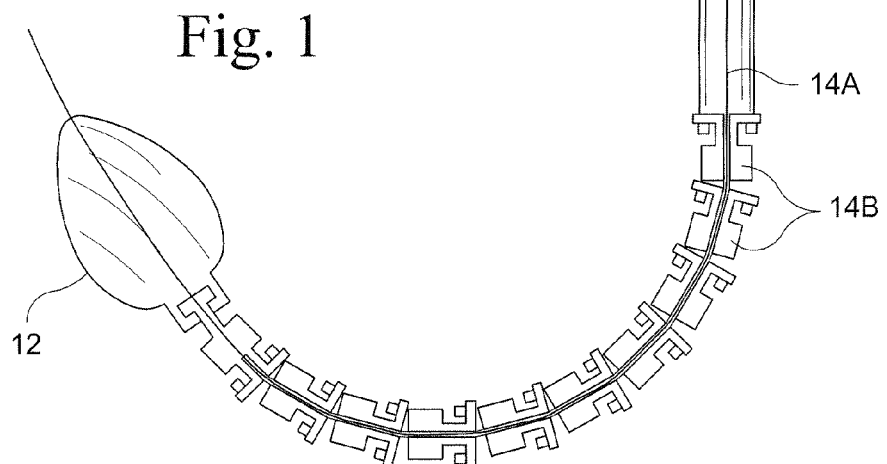
FIG. 2 shows the disc reamer of FIG. 1 positioned over a reamer guide wire.

Various embodiments of the intervertebral disc reamer will be described with reference to the drawings, where like elements are represented by like reference numerals. FIGS. 1 and 2 show an exemplary intervertebral disc reamer 10 of a preferred construction. Generally, the disc reamer 10 may be formed of a one-piece reamer head 12 with a shaft 14 such as a fixed but flexible shaft or a chain of shaft links 14B that are interlinked and movable relative to each other to impart flexibility, and a proximal shaft 14A.

Figure 8:
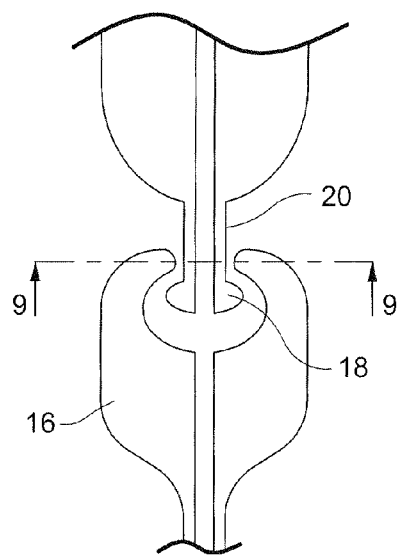
FIG. 8 is a close-up view of an exemplary chain articulation connection between shaft links.
Figure 9:
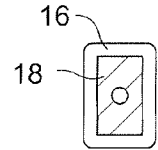
FIG. 9 is a cross-sectional view of an exemplary shaft link.
Figure 10:
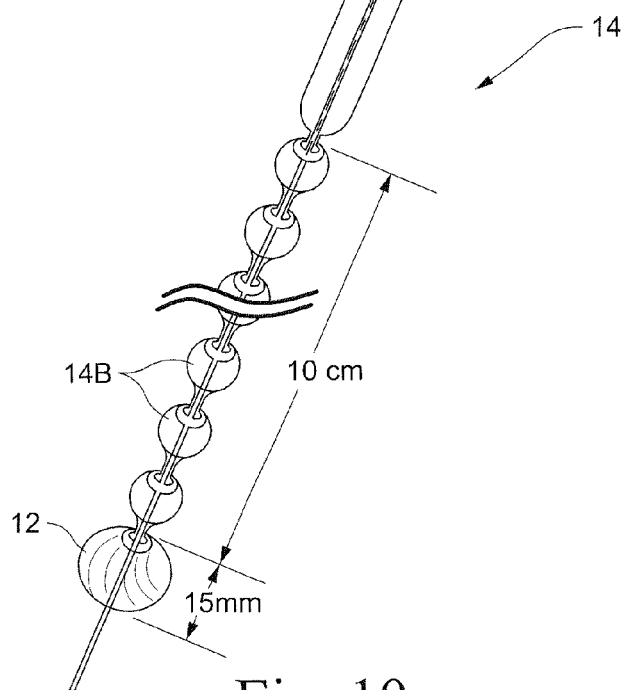
FIG. 10 illustrates an alternative construction for the disc reamer.

The reamer device 10 may be formed using different materials, including various metal alloys, plastic materials and the like. Generally, each of the shaft links 14B includes a link body 16 (FIG. 3), which is the female part of the piece into which the male part 18 of the articulating neighbor fits. The body 16 of the shaft links 14B is preferably oriented proximal but may be distal. A neck 20 is preferably attached to the distal part of the body 16 (at least adjacent the reamer head 12) but can be reversed such that it is proximal. The neck 20 is narrow to allow flexibility of the articulation. The neck 20 may be cylindrical or double cone shaped or the like with the narrowest diameter at its midpoint to allow greater range of motion of the articulation. The shaft links 14B may also be designed without a neck. The head 18 of each shaft link may be formed in multiple configurations, including a spherical shape that fits into a sphere of a larger diameter (see FIG. 10), preferably at the proximal end of the body of the adjoining member of the chain. The head 18 may be T-shaped (see male part 18 in FIG. 3) and fit into the female part (body 16) of the adjoining member. See also FIGS. 8 and 9. Alternatively, the link head may include a ring 14C attached to the distal and proximal surfaces of the body 16 that articulates with a corresponding ring on the adjoining member. This exemplary configuration is shown in FIG. 6.

Figures 13, 14:
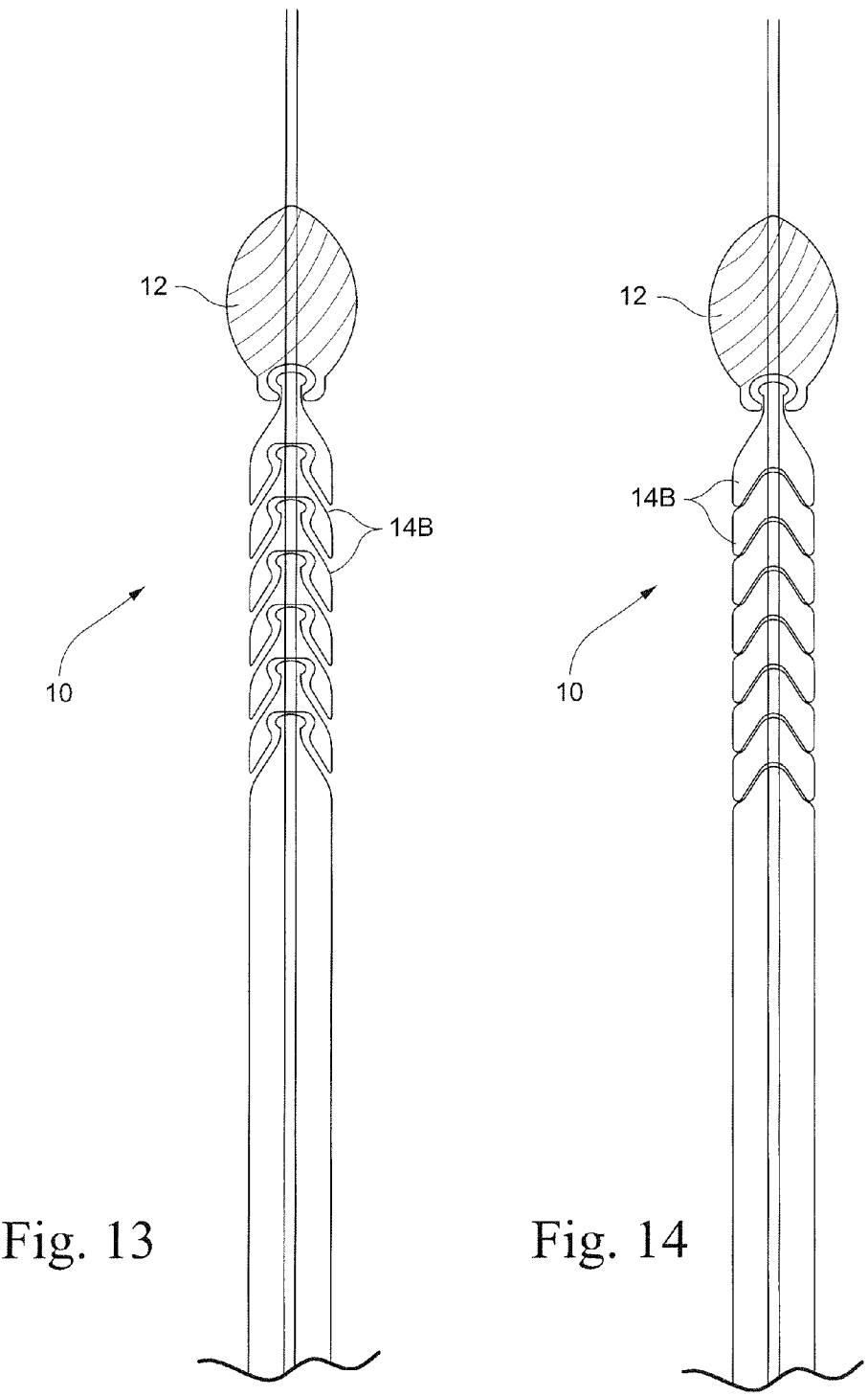
FIGS. 13 and 14 show yet another alternative construction for the disc reamer.

The shaft links 14B may have several possible body shapes, including spherical, cylindrical or scalloped proximally and distally, and the like. Preferably, the centers of all the shaft links 14B are cannulated. As noted, articulation of the pieces can be achieved in any number of possible designs as would be apparent to those of ordinary skill in the art. Additionally, the number of shaft links 14B can be varied to vary the shaft 14 length and/or arc radius of the disc reamer 10 in use (see FIG. 10). Moreover, as the shaft 14 itself can be used as part of the reaming process, the articulating pieces of the shaft 14 may have various options of surface finish including smooth, fluted and curved, fluted straight, a curved blade to propel the disc debris back as the reamer advances, and the like. With reference to FIGS. 13 and 14, the shaft links 14B may be contoured or otherwise shaped to bias their flexibility in certain planes while protecting the articulating structure from debris. The adjacent shaft links 14 are preferably movable in at least one plane relative to each other, but may be limited to a single plane if necessary to better control positioning of the disc reamer 10.

With continued reference to FIGS. 1 and 6, the proximal shaft 14A of the disc reamer is preferably formed of a cannulated metal but may alternatively be formed of a plastic material or the like. The proximal shaft 14A can be cylindrical shaped or rectangular with smooth edges or the like. A distal end of the proximal shaft 14A articulates with the most proximal member of the shaft links 14B through one of a spherical head (see FIG. 10), a T-shaped head (see FIGS. 1 and 3), rings (see FIG. 6) or the like. Once assembled and installed, the proximal shaft 14A is cooperable with an automated device such as a reamer driver or the like to rotate the reamer. The structure and operation of a reamer driver are known, and further details thereof will not be described.

A distal end of the shaft links 14 is connectable to the disc reamer head 12 via several options. For example, the head 12 and distal end of the shaft links may comprise a fixed articulation. Alternatively, the connection may accommodate movable articulation via a suitable joint such as a neck 20 of the shaft links 14B, a ball and socket joint, a T-shaped head articulating with the proximal female part of the reamer head, rings, or the like.

Figure 15:
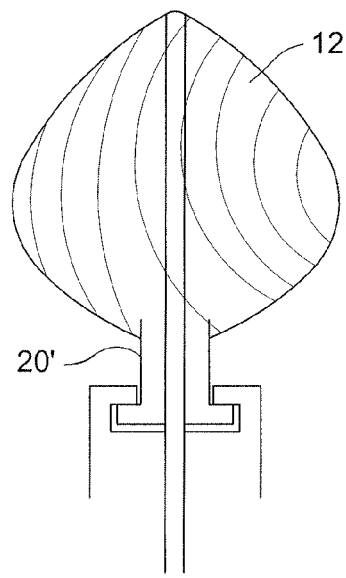
FIG. 15 is a close-up view of an exemplary reamer head.
Figure 16A:
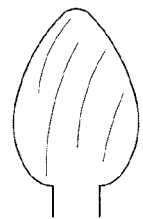
FIGS. 16A-16D show alternative exemplary configurations for the reamer head.
Figure 16B:
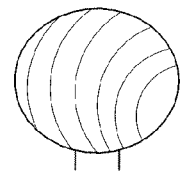
Figure 16C:
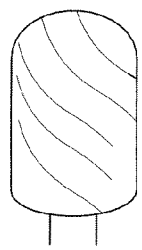
Figure 16D:
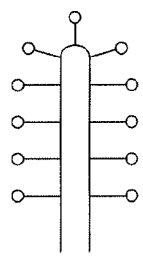

The disc reamer head 12 additionally includes several possible features including alternative shapes as conical (FIG. 16A), spherical (FIG. 16B), cylindrical (FIG. 16C) and the like. The surface finish may be roughened or include curved cutting blades or may alternatively be fit with flexible pins tipped with small metal balls (so-called mini wrecking balls—see FIGS. 5 and 16D). FIG. 15 is a close-up view of an exemplary reamer head 12. In the exemplary shape shown in FIG. 15, the widest diameter of the reamer head 12 is generally centrally disposed and can vary by application from less than 5 mm to more than 12 mm. The reamer head 12 is readily exchangeable to accommodate varying applications. As shown in FIG. 15, the neck 20' serving as connecting structure between the head 12 and the distal shaft link 14B may form part of the head 12 rather than the shaft link 14B.

Figure 11:
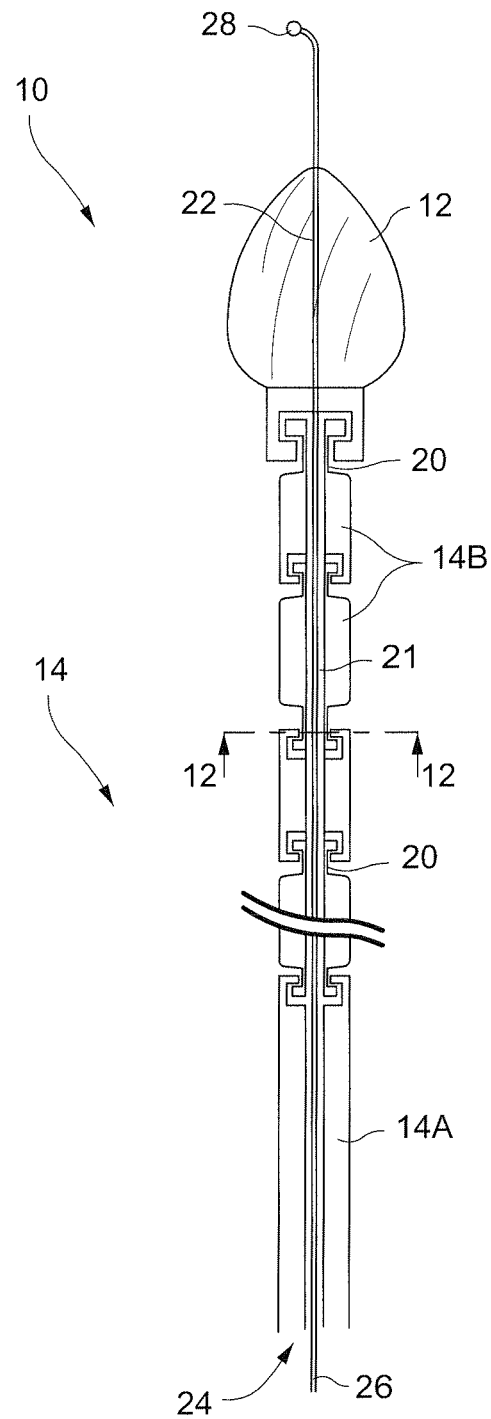
FIGS. 11 and 12 show another alternative construction for the disc reamer.
Figure 12:
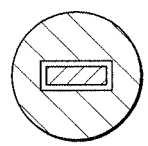
Figure 17:
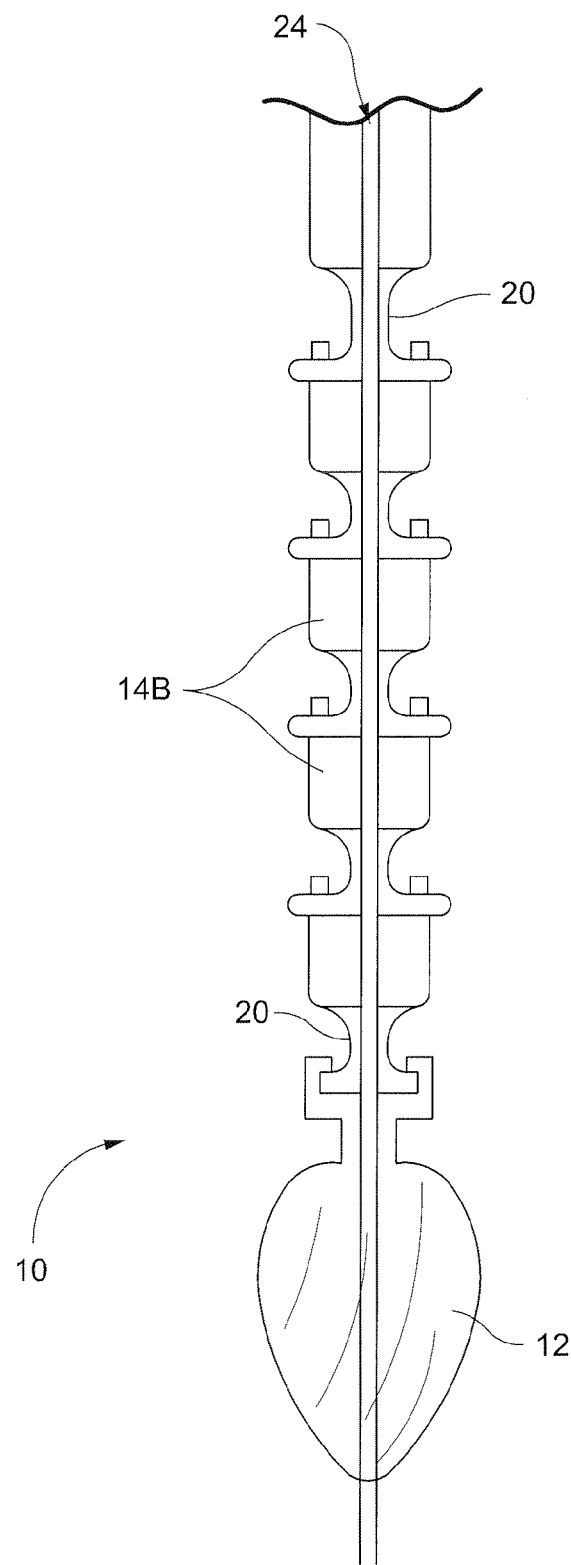
FIG. 17 shows yet another exemplary configuration for the disc reamer.

FIGS. 11 and 12 and FIG. 17 show exemplary configurations for the disc reamer 10. The shaft 14 is made up of shaft links 14B and a proximal shaft 14A. The reamer head 12 is coupled with a distal end of the distal shaft link 14B via a movable connection. As shown, the shaft 14 includes cannulated pieces that define a shaft channel 21. The reamer head 12 is similarly cannulated and includes a reamer channel 22. As shown in FIG. 11, when constructed, the shaft channel 21 and the reamer channel 22 are aligned to define a continuous guide wire channel 24 for the disc reamer 10.

The guide wire channel 24 is sized to accommodate a reamer guide 26 that is preferably formed of a flexible non-deforming material. In particular, the reamer guide 26 may be formed of a metal alloy that is strong yet flexible and non-deforming. A tip 28 of the reamer guide 26 may be simply plain or may include structure shaped as a ball, a bullet, a curve, and the like. With reference to FIGS. 7A and 7B, in one embodiment, the reamer guide 26 utilizes a "memory" material where the reamer guide 26 has a first shape prior to insertion and a second shape after warming to the patient's body temperature. FIG. 7A shows a generally straight guide 26 prior to insertion, and FIG. 7B shows a significantly more curved orientation after warming to the patient's body temperature.

In order to insert the intervertebral disc reamer 10 into proper placement for use, it is possible to secure one or more threaded cannulas into a patient's disc space. The threads of the cannulas are secured directly into the vertebral endplates. The reamer guide 26 is introduced into the disc space through the previously-placed threaded cannulas under X-ray control. Once the satisfactory position of the guide wire 26 within the disc space has been confirmed, the disc reamer 10 is inserted over the guide wire 26, and reaming is performed while visualizing the progress of the procedure under image intensifier control. An irrigation and suction system may be attached to the device to ensure removal of the disc debris simultaneously as the disc debridement. Since the disc reamer 10 is flexible, the disc reamer follows an orientation of the guide wire.

The disc reamer of the described embodiments improves the quality of disc removal and endplate preparation while minimizing the trauma of surgery, minimizing blood loss, and markedly reducing surgical time. Using the threaded cannulas that are locked into the vertebral endplates prevents operation of the reamer outside of the disc space. Additionally, use of a flexible non-deforming guide wire controls the direction and depth of reaming under fluoroscopic control, thereby ensuring safe use of the device during surgery.

The described embodiments relate to a flexible intervertebral disc reamer. One problem encountered with the described disc reamer is that it involves repeated passages of the reamer with each subsequent passage using a larger diameter reamer head. The limitation of the non-expandable reamer is its risk of damage to nerve roots or the dura as larger instruments are inserted to prepare discs with the heights taller than 6.00 mm. Using larger cannulas for access to such discs may cause injury to the nerve roots. Utilizing cannulas smaller than the disc heights will result in less than optimal end-plate preparation.

An improvement to the described embodiments thus lies in an expandable intervertebral disc reamer, which fulfills the requirements of the least invasive spine surgery while avoiding the risk of suboptimal disc space and end-plate preparation. In a preferred embodiment, the EIVDR (Expandable Inter-Vertebral Disc Reamer) has the following features:
1. Flexible shaft
2. Cannulation of the shaft and the reamer head
3. The reamer head is made of a metal alloy
4. The reamer head is split longitudinally into four or more parts each carrying a cutting blade on its exterior surface
5. The interior of the head is cannulated and the cutting parts are apposed to each other in the unexpanded position, leaving a cylindrical or conical space in its central axis.
6. Threaded expander that runs down the center of the shaft to the base of the reamer head. The expander's threaded head may be conical with a narrow tip and wide base such that as it is threaded down the center of the reamer head, the latter expands as the expander advances down its center. The expander is also cannulated so that it can be inserted into the disc space over the guide wire along with the expandable reamer.
7. The reamer shaft and head fit into the intervertebral disc through the access cannula. The cannula may be armed with an irrigation system alone or irrigation/suction system to remove the debris from the disc space.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. An intervertebral disc reamer comprising:
 a flexible shaft having a shaft channel; and
 a reamer head attached to the flexible shaft by a movable joint connection such that the reamer head is movable relative to the flexible shaft, the reamer head having a reamer channel, wherein the shaft channel and the reamer channel are aligned to define a continuous guide wire channel for the disc reamer,
 wherein the flexible shaft comprises a plurality of shaft links connectable one to another, and wherein the shaft links have a surface finish that propels disc debris back as the reamer head is advanced.

2. An intervertebral disc reamer according to claim 1, wherein the flexible shaft comprises a one-piece proximal shaft attached to a chain of the shaft links.

3. An intervertebral disc reamer according to claim 1, wherein a distal one of the shaft links is coupled with the reamer head, and wherein adjacent shaft links are movable in at least one plane relative to each other.

4. An intervertebral disc reamer according to claim 3, wherein the shaft links are shaped as one of spherical, cylindrical and scalloped proximally and distally.

5. An intervertebral disc reamer according to claim 4, wherein each of the shaft links is cannulated.

6. An intervertebral disc reamer according to claim 1, wherein the adjacent shaft links are contoured to bias flexibility in at least one predefined plane while protecting the adjacent shaft links from debris.

7. An intervertebral disc reamer according to claim 1, wherein the reamer head is attached to the flexible shaft via a neck, the neck having a narrow cross-section so as to facilitate flexibility of articulation.

8. An intervertebral disc reamer according to claim 1, wherein the reamer head is shaped as one of cylindrical, conical and spherical.

9. An intervertebral disc reamer according to claim 8, wherein the reamer head has a surface finish as one of roughened, curved into cutting blades, and flexible pins tipped with small metal balls.

10. An intervertebral disc reamer according to claim 8, wherein the movable joint connection comprises one of a ball and socket connection and a T-shaped slot or bar coupled with a corresponding T-shaped bar or slot in a distal end of the flexible shaft.

11. An intervertebral disc reamer according to claim 1, further comprising a reamer guide sized to fit in the guide wire channel, the reamer guide being formed of a flexible non-deforming construction.

12. An intervertebral disc reamer according to claim 1, wherein the flexible shaft includes circumferential channels along a length of the flexible shaft.

13. An intervertebral disc reamer according to claim 1, wherein the shaft links include channels.

14. An intervertebral disc reamer according to claim 1, wherein each of the shaft links comprises a leading end facing the reamer head and a trailing end facing an opposite direction, and wherein the leading end is narrower than the trailing end.

15. An intervertebral disc reamer according to claim 14, wherein the leading end defines a male connecting part, and wherein the trailing end defines a female receiving part engageable with the male connecting part.

16. An intervertebral disc reamer comprising:
 a flexible shaft formed of a plurality of cannulated shaft links connectable one to another, the cannulated shaft links defining a shaft channel;
 a neck movably secured to a distal shaft link of the flexible shaft; and
 a reamer head attached to the flexible shaft via the neck by a movable joint connection such that the reamer head is movable relative to the flexible shaft, the reamer head having a reamer channel, wherein the shaft channel and the reamer channel are aligned to define a continuous guide wire channel for the disc reamer,
wherein the cannulated shaft links have a surface finish that propels disc debris back as the reamer head is advanced.

* * * * *